US00PP27160P3

(12) United States Plant Patent
Ilsink

(10) Patent No.: US PP27,160 P3
(45) Date of Patent: Sep. 20, 2016

(54) SHRUB ROSE PLANT NAMED 'INTROS04'

(50) Latin Name: *Rosa hybrida*
Varietal Denomination: IntRos04

(71) Applicant: Robert Ilsink, Leersum (NL)

(72) Inventor: Robert Ilsink, Leersum (NL)

(73) Assignee: Interplant Roses B.V. (NL)

( * ) Notice: Subject to any disclaimer, the term of this patent is extended or adjusted under 35 U.S.C. 154(b) by 110 days.

(21) Appl. No.: 14/120,792

(22) Filed: Jun. 27, 2014

(65) Prior Publication Data

US 2015/0382525 P1 Dec. 31, 2015

(51) Int. Cl.
*A01H 5/02* (2006.01)

(52) U.S. Cl.
USPC ..... Plt./104

(58) Field of Classification Search
USPC ..... Plt./101, 104
See application file for complete search history.

(56) References Cited

PUBLICATIONS

Internet retrieval for www.preb.com/releases/2013/9/prweb11114553.htm on Dec. 3, 2015. (4 pgs total).*
Internet retrieval for http://shop.monrovia.com/sweetspottmrubyrose.html on Dec. 4, 2015 (2 pgs total).*

* cited by examiner

*Primary Examiner* — Susan McCormick Ewoldt
(74) *Attorney, Agent, or Firm* — Cassandra Bright

(57) ABSTRACT

A new and distinct *Rosa* cultivar named 'IntRos04' is disclosed, characterized by abundant flowering, compact form and unique flower coloration of yellow with a red center eye. The new variety is a *Rosa*, normally produced as an outdoor garden or container plant.

3 Drawing Sheets

Latin name of the genus and species: *Rosa hybrida.*
Variety denomination: 'IntRos04'.

BACKGROUND OF THE INVENTION

The new *Rosa* cultivar is a product of a planned breeding program conducted by the inventor, Robert Ilsink, in Leersum, Netherlands. The objective of the breeding program was to produce new *Rosa* varieties for ornamental commercial applications. The cross resulting in this new variety was made during April of 2006.

The seed parent is the unpatented, proprietary variety referred to as *Rosa* 'INTERBYLONSTRA'. The pollen parent is the commercial variety referred to as *Rosa* 'INTERBYLONERI'. The new variety was discovered in April of 2007 by the inventor in a group of seedlings resulting from the 2006 crossing, in a research greenhouse in Leersum, Netherlands.

Asexual reproduction of the new cultivar was performed by vegetative cuttings. This was first performed at a research greenhouse in Leersum, Netherlands in Summer of 2008 and has shown that the unique features of this cultivar are stable and reproduced true to type in more than 6 successive generations.

SUMMARY OF THE INVENTION

The cultivar 'IntRos04' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IntRos04'

These characteristics in combination distinguish 'IntRos04' as a new and distinct *Rosa* cultivar:

1. Red spot in center of flower.
2. Compact size.
3. Abundant flowering.
4. Good disease resistance.

Plants of the new cultivar 'IntRos04' are similar to plants of the seed parent, *Rosa* 'INTERBYLONSTRA' in most horticultural characteristics, however, plants of the new cultivar 'IntRos04' differ in the following:

1. Light yellow flower color. The seed parent has a golden yellow colored flower.
2. Approximately 5 to 12 petals per flower. The seed parent has approximately 20 petals per flower.

Plants of the new cultivar 'IntRos04' are similar to plants of the pollen parent; *Rosa* 'INTERBYLONERI' in most horticultural characteristics, however, plants of the new cultivar 'IntRos04' differ in the following;

1. Light yellow flower color. The pollen parent has a pink and white colored flower.

COMMERCIAL COMPARISON

Plants of the new cultivar 'IntRos04' can also be compared to the commercial variety *Rosa* 'Interbylonbab', unpatented. These varieties are similar in most horticultural characteristics; however 'IntRos04' differs in the following:

1. Larger and more intense red blotch at the base of the petal.

BRIEF DESCRIPTION OF THE PHOTOGRAPHS

The accompanying photograph in FIG. 1 illustrates in full color a typical plant of 'IntRos04' grown in an approximately 2 gallon nursery pot. Age of the plant photographed is approximately 2 years.

Figure 1:
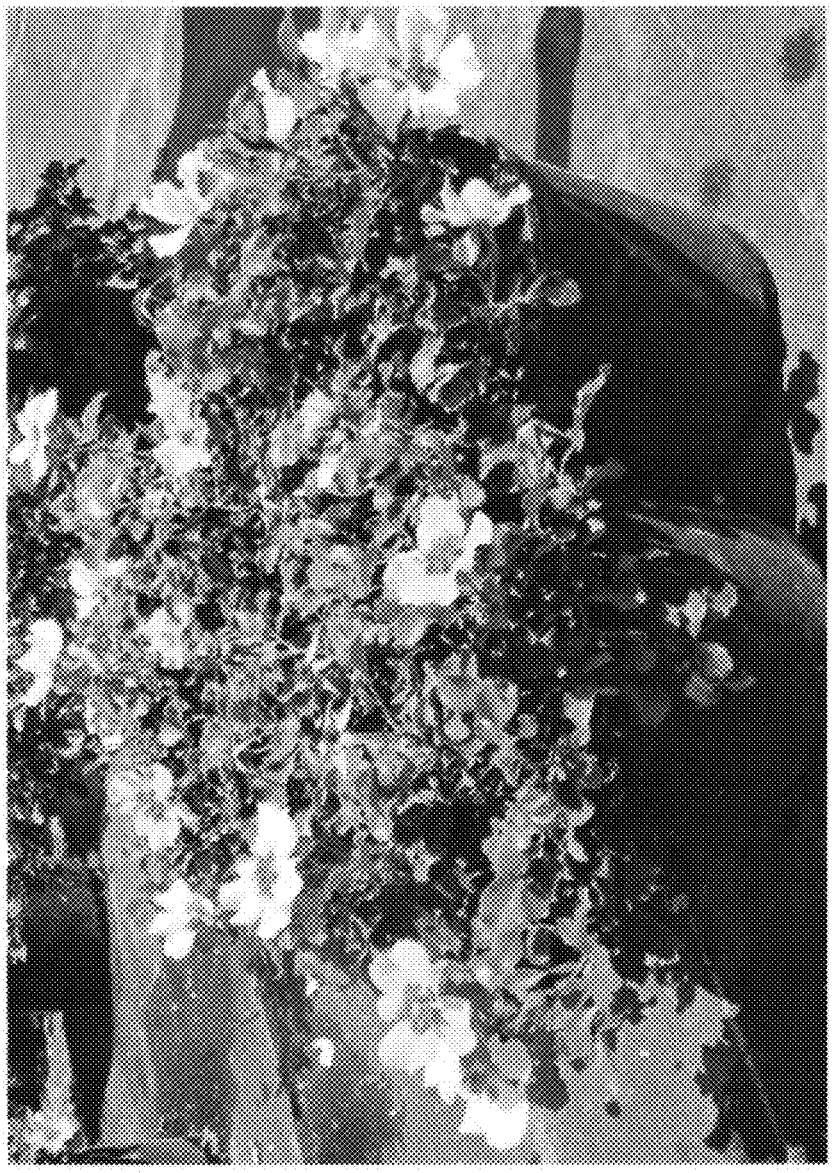
Figure 2:
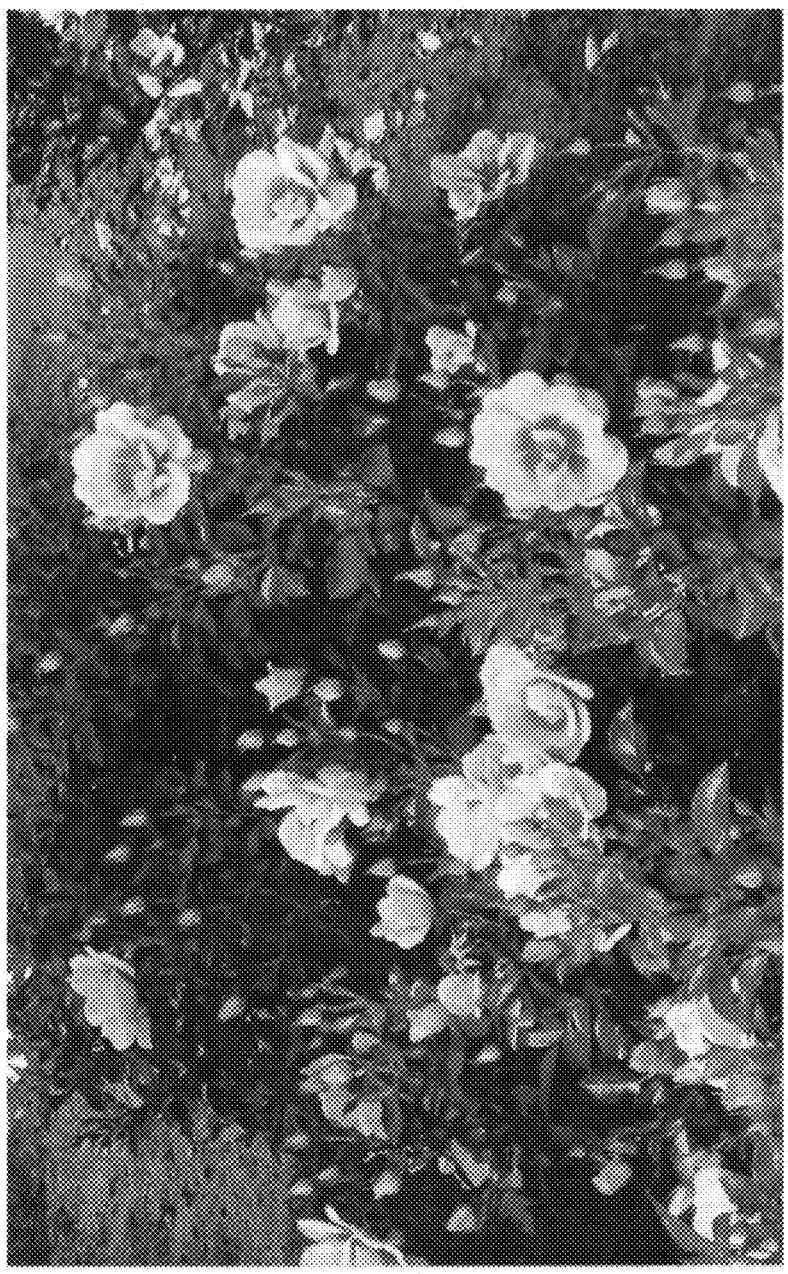
FIG. 2 illustrates a close up of multiple flowers, in various stages of maturity.
Figure 3:
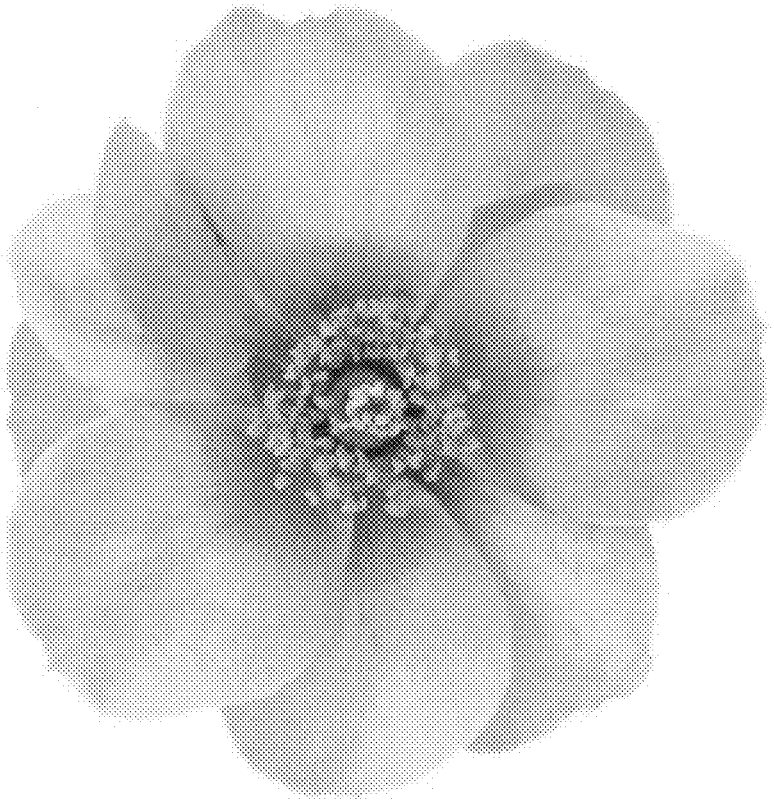
FIG. 3 illustrates a close up of a single mature flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'IntRos04' plants grown outdoors in, Leersum, Netherlands. The growing temperature ranged from approximately 0° C. to 28° C. during the day and from approximately −5° C. to 18° C. during the night. General light conditions are bright, normal sunlight. Measurements and numerical values represent averages of typical plant types.

Botanical classification: *Rosa hybrida* 'IntRos04'.

Commercial classification: Shrub rose.

PROPAGATION

Time to initiate roots: About 15 days at approximately 20° C.

Time to produce a rooted cutting: About 35 days at approximately 20° C.

PLANT

Age of plant described: Approximately 2 years.

Growth habit: Compact spreading shrub type rose.

In a container or in the ground: In container.

Height: 400 mm (40 cm).

Plant spread: 400 mm (40 cm).

Rootstock: Own root.

Growth rate: Approximately 2 years to reach 0.4 meters.

Branching characteristics: Sympodial branching.

Length of primary lateral branches: Approximately 40 cm.

Diameter of lateral branches: Approximately 1 cm.

Quantity of lateral branches: Numerous.

Branching arrangement: Branching from every axillary bud possible.

Branches — Young wood:

- *Diameter*.—Approximately 0.5 cm.
- *Texture*.—Herbaceous; glossy with anthocyanin coloration.
- *Approximately density/quantity of thorns*.—Dense.
- *Color*.—Near Purple RHS 79D.

Branches — Old wood:

- *Diameter*.—Approximately 1.0 cm, after 2 years.
- *Color*.—Near Green RHS 134B.
- *Texture*.—Woody; semi glossy.
- *Approximately density/quantity of thorns*.—Numerous.
- *Color of thorns*.—Red purple, closest to 60A.

FOLIAGE

Leaf:

- *Arrangement*.—Alternate.
- *Quantity*.—Approximately 4 per main branch.
- *Average length*.—Approximately 12 cm.
- *Average width*.—Approximately 8 cm.

Leaflet:

- *Quantity*.—Approximately 5 per leaf.
- *Average length*.—Approximately 4 cm.
- *Average width*.—Approximately 2.5 cm.
- *Shape of blade*.—Oval.
- *Apex*.—Pointed.
- *Base*.—Rounded.
- *Margin*.—Serrated.
- *Texture of top surface*.—Glabrous.
- *Appearance of top surface*.—Semi glossy.
- *Appearance of bottom surface*.—Matte.
- *Texture of top surface*.—Non-pubescent.
- *Texture of bottom surface*.—Non-pubescent.
- *Color*.—Young foliage upper side: Near Green RHS 140B. Young foliage under side: Near Green RHS 140B. Mature foliage upper side: Near Green RHS 126B. Mature foliage under side: Near Green RHS 126B.
- *Venation*.—Type: Reticulate. Venation color upper side: Indistinguishable from leaf blade. Venation color under side: Indistinguishable from leaf blade.

FLOWER

Natural flowering season: Spring until Autumn.

Begins flowering after how many years/months: 2 months.

Inflorescence type and habit: Raceme.

Rate of flower opening: Approximately 1 day from bud to fully opened flower.

Flower longevity on plant: 4 days, after fully opened.

Quantity of flowers: 3-5.

Inflorescence size:

- *Diameter*.—Approximately 12 cm.
- *Length*.—Approximately 12 cm.

Individual flower size:

- *Diameter*.—Approximately 4.4 to 5.6 cm.
- *Depth*.—Approximately 2.0 cm.

Peduncle:

- *Length*.—2 cm.
- *Diameter*.—0.3 cm.
- *Color*.—Near RHS Green 141C.

Petals:

- *Petal arrangement*.—Rotate overlapping.
- *Size*.—Length: 2 cm. Width: 2 cm. Shape: Broad ovate. Margin: No reflexing. Apex: Undulating. Base: Obtuse. Petal quantity: 5 to 12. 10 to 12 most common under brighter light conditions. Texture: Soft.

Color:

Petals:

- *When opening*.—Upper surface: Near Yellow RHS 4C, base near Red 45C. Lower surface: Near Yellow RHS 4C.
- *Fully opened*.—Upper surface: Near Yellow RHS 4C, base near Red 45A. Lower surface: Near Yellow RHS 4C. Color Changes when aging: Changing to Yellow-White 155D, center blotch Red 46B.

Bud:

- *Shape*.—Ovate.
- *Length*.—Approximately 2 cm.
- *Diameter*.—Approximately 1 cm.
- *Color*.—Near Yellow RHS 4C, flushed near tip with Red 46B.

Sepals:

- *Length*.—2 cm.
- *Width*.—0.4 cm.

*Shape*.—Narrow deltoid.

*Color*.—Interior Surface: Near Green RHS 137A. Exterior Surface: Near Green RHS 137A.

*Texture*.—Non-pubescent.

*Fragrance*.—None.

REPRODUCTIVE ORGANS

Stamens:

*Filament length*.—Approximately 0.5 cm.

*Filament color*.—Near Yellow RHS 7A.

Anthers:

*Length*.—0.2 cm.

*Shape*.—Linear.

*Color*.—Near Yellow-Orange RHS 16C.

*Pollen*.—Color: Near Yellow 9A. Quantity: Abundant.

Pistil:

*Style*.—Length: Approximately 0.2 cm. Color: Near Yellow RHS 9D.

*Stigma*.—Shape: Linear. Color: Near Yellow RHS 9D.

OTHER CHARACTERISTICS

Seeds and fruits: Not observed to date.

Disease/pest resistance: Good overall disease resistance to normal pests and diseases typical of garden roses.

What is claimed is:

1. A new and distinct cultivar of *Rosa* plant named 'IntRos04' as herein illustrated and described.

* * * * *